United States Patent
Bornzin et al.

(10) Patent No.: US 7,233,827 B1
(45) Date of Patent: *Jun. 19, 2007

(54) IMPLANTABLE CARDIAC STIMULATION DEVICE WITH AUTOMATIC EVOKED RESPONSE SENSING ELECTRODE CONFIGURATION SELECTION AND METHOD

(75) Inventors: Gene A. Bornzin, Simi Valley, CA (US); Joseph J. Florio, La Canada, CA (US); Laurence S. Sloman, Los Angeles, CA (US); Brian M. Mann, Beverly Hills, CA (US); Jason A. Sholder, Fort Lee, NJ (US)

(73) Assignee: Pacesetter, Inc., Sylmar, CA (US)

( * ) Notice: Subject to any disclaimer, the term of this patent is extended or adjusted under 35 U.S.C. 154(b) by 352 days.

This patent is subject to a terminal disclaimer.

(21) Appl. No.: 10/865,124

(22) Filed: Jun. 9, 2004

Related U.S. Application Data

(63) Continuation of application No. 09/655,438, filed on Sep. 5, 2000, now Pat. No. 6,782,291.

(51) Int. Cl.
*A61N 1/365* (2006.01)
(52) U.S. Cl. ...................................... 607/28
(58) Field of Classification Search ................... 607/28
See application file for complete search history.

(56) References Cited

U.S. PATENT DOCUMENTS

| | | | |
|---|---|---|---|
| 4,686,988 A | 8/1987 | Sholder | 128/419 |
| 4,708,142 A | 11/1987 | DeCote, Jr. | 128/419 |
| 4,712,555 A | 12/1987 | Thornander et al. | 128/419 |
| 4,729,376 A | 3/1988 | DeCote, Jr. | 128/419 |
| 4,940,052 A | 7/1990 | Mann et al. | 128/149 |
| 4,944,298 A | 7/1990 | Sholder | 128/419 |
| 4,969,467 A | 11/1990 | Callaghan et al. | 128/149 |
| 4,991,583 A | 2/1991 | Silvian | 128/419 |
| 5,003,975 A | 4/1991 | Hafelfinger et al. | 128/419 |
| 5,324,310 A * | 6/1994 | Greeninger et al. | 607/28 |
| 5,350,410 A * | 9/1994 | Kleks et al. | 607/28 |
| 5,411,528 A | 5/1995 | Miller et al. | 607/5 |
| 5,466,254 A | 11/1995 | Helland | 607/123 |
| 5,855,594 A * | 1/1999 | Olive et al. | 607/28 |
| 5,873,898 A | 2/1999 | Hemming et al. | 607/28 |
| 6,175,766 B1 * | 1/2001 | Bornzin et al. | 607/28 |
| 6,263,244 B1 * | 7/2001 | Mann et al. | 607/28 |
| 6,363,281 B1 * | 3/2002 | Zhu et al. | 607/28 |
| 6,782,291 B1 * | 8/2004 | Bornzin et al. | 607/28 |

FOREIGN PATENT DOCUMENTS

WO    WO 00/33915    6/2000

* cited by examiner

*Primary Examiner*—Carl Layno
*Assistant Examiner*—Eric D. Bertram

(57) ABSTRACT

An implantable cardiac stimulation device applies pacing stimulation pulses to a heart and senses evoked responses to the pacing stimulation pulses. A pulse generator applies the stimulation pacing pulses to the heart in accordance with a pacing configuration. A sensor control selects an evoked response sensing electrode configuration from among a plurality of evoked response sensing electrode configurations in response to the pacing configuration. A sensor is then programmed to sense the evoked responses with the selected evoked response sensing electrode configuration. In accordance with a preferred embodiment, signal-to-noise ratios obtained with the various electrode configurations are used to select a best electrode configuration for sensing evoked responses.

12 Claims, 3 Drawing Sheets

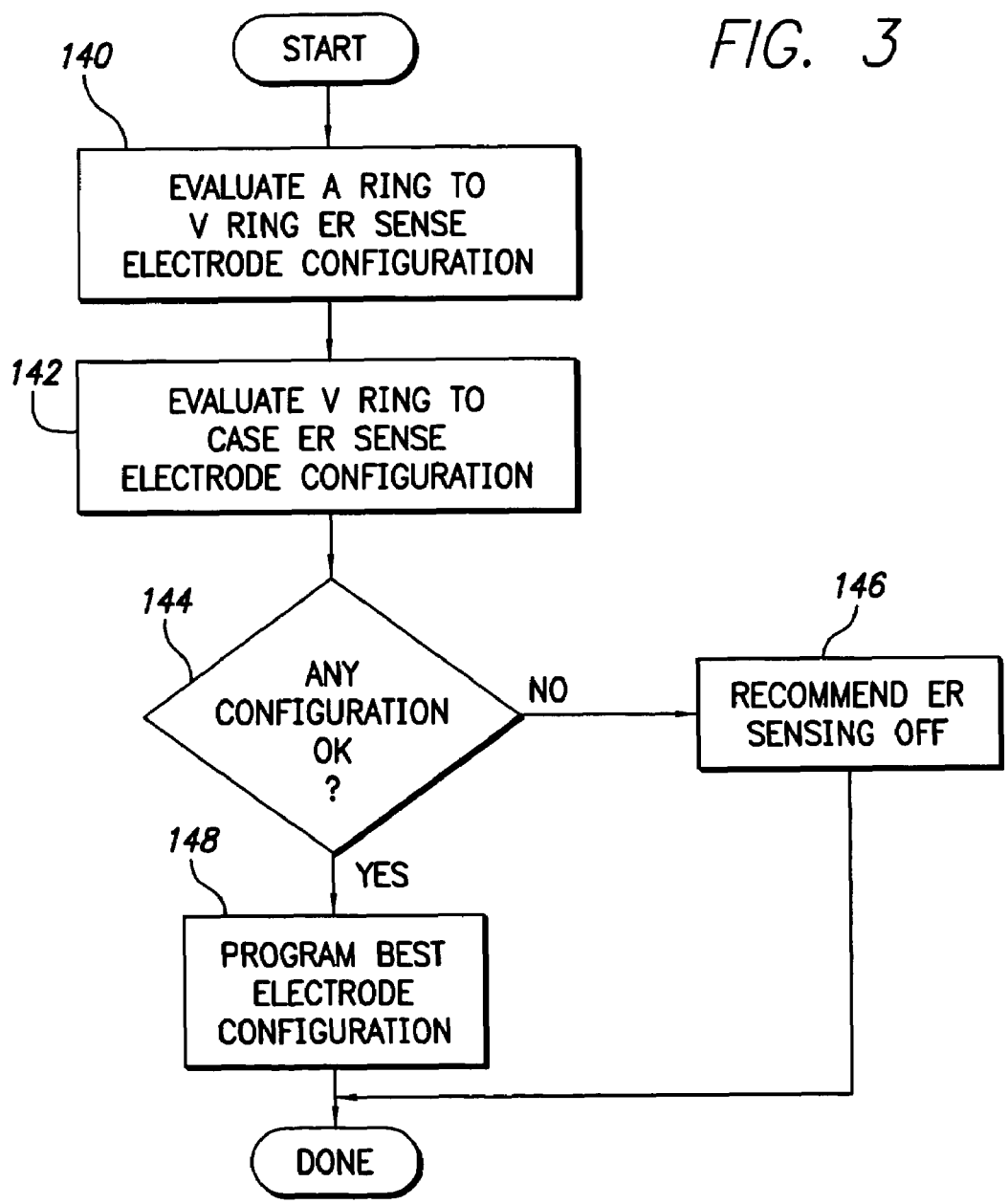

IMPLANTABLE CARDIAC STIMULATION DEVICE WITH AUTOMATIC EVOKED RESPONSE SENSING ELECTRODE CONFIGURATION SELECTION AND METHOD

CROSS REFERENCE TO RELATED APPLICATIONS

This application is a continuation of U.S. patent application Ser. No. 09/655,438, filed Sep. 5, 2000, now U.S. Pat. No. 6,782,291.

FIELD OF THE INVENTION

The present invention generally relates to an implantable cardiac stimulation device. The present invention is more particularly directed to such a device and method which provides automatic selection of evoked response sensing electrode configurations.

BACKGROUND OF THE INVENTION

Implantable cardiac stimulation devices are well known in the art. Such devices apply electrical stimulation pulses to one or more chambers of the heart. The energies of the applied stimulation pulses are selected so as to be above the pacing energy stimulation threshold of the respective heart chamber to cause the cardiac tissue of that chamber to depolarize. Depolarization of the cardiac tissue of the respective chamber in turn causes the respective chamber heart muscle to contract. In this manner, the required pumping action of the heart is sustained.

It is therefore desirable to ascertain the pacing energy stimulation threshold of a heart chamber to be paced. A pacing energy may then be selected which is above the threshold to assure reliable pacing.

When a pacing pulse is effective in causing depolarization or contraction of the heart muscle, it is referred to as "capture" of the heart. Conversely, when a pacing pulse is ineffective in causing depolarization or contraction of the heart muscle, it is referred to as "lack of capture" of the heart.

An electrogram (EGM), as is also well known in the art, is an electrical signal representing the electrical activity of a heart muscle. The electrical manifestation of lack of capture in a heart muscle is typically a negative deflection in the electrogram baseline. This is referred to as polarization (POL). The electrical manifestation of capture in a heart muscle is typically an exaggerated biphasic deflection in the EGM. This is generally referred to as the evoked response plus polarization (ER+POL).

When a cardiac stimulation device performs a pacing energy stimulation threshold search or test, it applies a succession of test pacing pulses at a basic rate. The energy of each successive pacing pulse is reduced by a known amount and capture is verified following each pulse. Capture may be verified by detecting the evoked response.

Each stimulation includes a pair of pulses, a primary pulse and a subsequent backup pulse. The stimulation pulses of each pair are timed such that, if the primary pulse captures, the backup pulse will be delivered during the refractory period to provide a measure of polarization. The polarization waveform is subtracted from the evoked response plus polarization waveform to determine if capture occurred.

Sensing of evoked responses is therefore useful for capture verification and threshold assessment. Unfortunately, sensing of evoked responses is often difficult. Polarization after potentials tend to obscure the evoked responses when leads are used which have polarizing electrodes, such as electrodes formed of polarized platinum. Further, a number of leads, like active fixation screw-in leads continue to include electrodes formed of polarizing materials. Still further, leads that are retained for further use at device replacement tend be early generation leads having polarizing electrodes.

The present invention addresses the issues of sensing evoked responses. More specifically, as will be seen hereafter, the present invention provides for the automatic selection of the best evoked response sensing electrode configuration from among the most propitious evoked response sensing electrode configurations offered by a cardiac stimulation system.

SUMMARY OF THE INVENTION

The present invention provides an implantable cardiac stimulation device and method wherein pacing stimulation pulses are applied to a heart and evoked responses to the stimulation pulses are sensed utilizing an automatically selected evoked response sensing electrode configuration.

A plurality of available evoked response sensing electrode configurations are stored in a memory. A sensor control selects an evoked response sensing electrode configuration from among the stored configuration in response to the current pacing configuration. The pacing configuration may be defined by device type, pacing lead type, and/or electrode implant sites.

When more than one evoked response sensing electrode configuration is available for a given pacing configuration, each available evoked response sensing electrode configuration is evaluated by the measurement of a common sensing characteristic, such as signal-to-noise ratio. The evoked response sensing electrode configuration yielding the greatest sensing characteristic measurement is then selected and programmed into the device. Evoked response sensing electrode configurations may be selected for both ventricular and atrial evoked responses in accordance with the present invention.

The evoked response sensing electrode configuration evaluation is preferably implemented by a processor. When the measured sensing characteristic is signal-to-noise ratio, the processor is preferably programmed to measure the evoked response plus polarization resulting from capture by a first stimulation pulse and subtracting from it a measured polarization in response to a second stimulation pulse delivered during a refractory period. The electrode configuration yielding the greatest difference may then be selected and programmed into the device. Thereafter, whenever evoked responses are to be sensed, the processor and a switch bank couple the best electrode configuration for sensing evoked responses to a sensing circuit.

BRIEF DESCRIPTION OF THE DRAWINGS

Further features and advantages of the present invention may be more readily understood by reference to the following description taken in conjunction with the accompanying drawings, in which:

FIG. 3 is a flow chart illustrating the operation of the present invention in connection with, by way of example, a specific exemplary pacing configuration, for selecting an evoked response sensing electrode configuration from among a plurality of available evoked response sensing electrode configurations, in accordance with the present invention.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
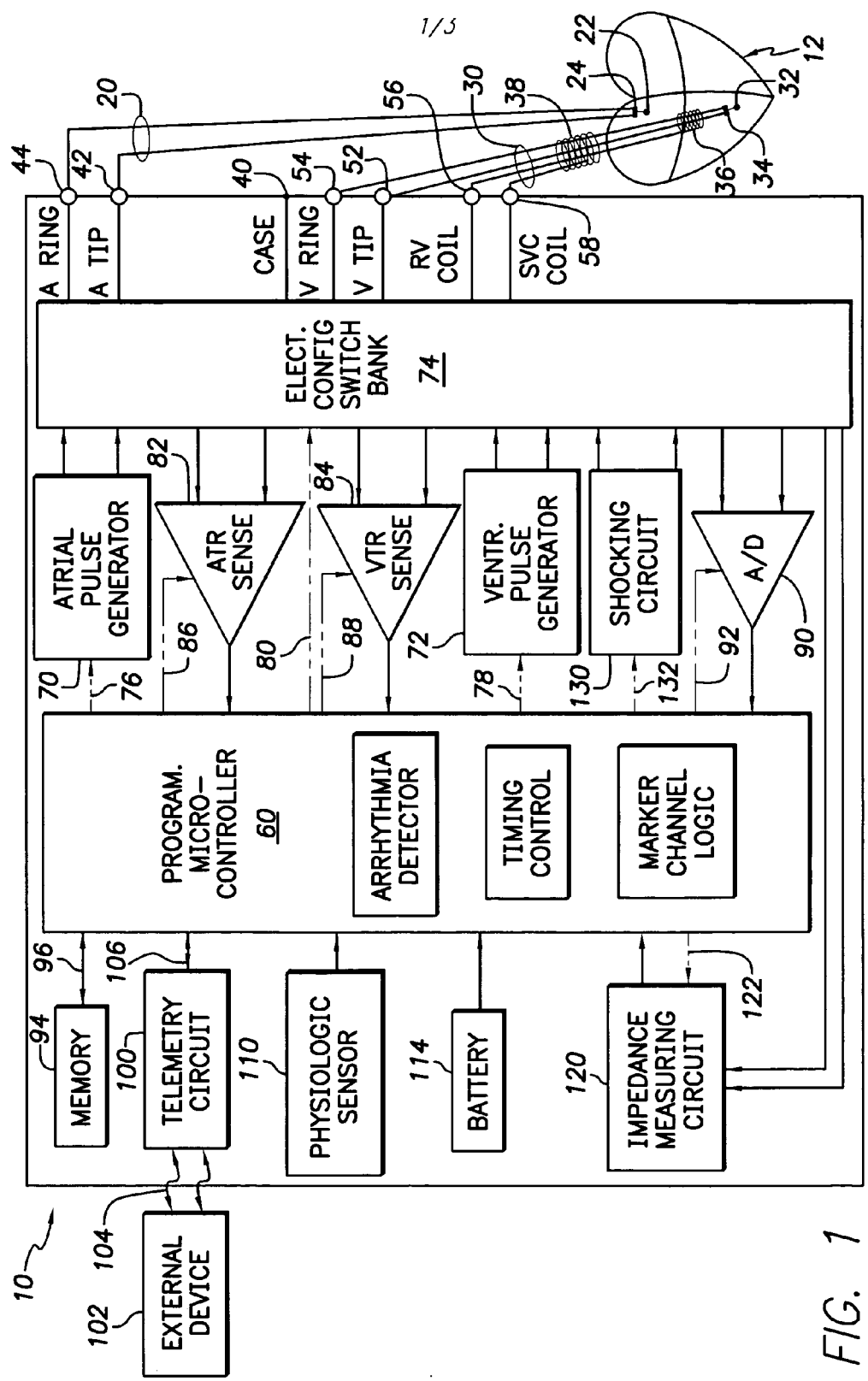
FIG. 1 is a functional block diagram of a dual-chamber implantable stimulation device illustrating the basic elements of a stimulation device which can provide cardioversion, defibrillation and pacing stimulation.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20. The lead 20 has an atrial tip electrode 22 and an atrial ring electrode 24. The ring electrode 24 is typically implanted in the patient's atrial appendage.

The stimulation device 10 is also shown in electrical communication with the patient's heart 12 by way of an implantable ventricular lead 30. The lead 30, in this embodiment, has a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. Pat. No. 5,466,254, "Coronary Sinus Lead With Atrial Sensing Capability" (Helland), which patent is hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, along or in combination with one of the coil electrodes, 36 and 38. For convenience, the names of the electrodes are shown next to the terminals.

At the core of the stimulation device 10 is a programmable microcontroller 60 which controls the various modes of stimulation therapy. As is will known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. Representative types of control circuitry that may be used with the invention include the microprocessor-based control system of U.S. Pat. No. 4,940,052 (Mann et al.), the state-machine of U.S. Pat. Nos. 4,712,555 (Thornander et al.) and 4,944,298 (Sholder). For a more detailed description of the various timing intervals used within the stimulation device and their inter-relationship, see U.S. Pat. No. 4,788,980 (Mann et al.). The '052, '555, '298d and '980 patents are incorporated herein by reference.

As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses (e.g., pacing rate and atrio-ventricular (AV) delay), as well as keeping track of the timing of any refractory periods, PVARP intervals, noise detection windows, evoked response windows, alert intervals, marker channel timing, etc., that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art.

An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers. The sense amplifiers, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sense amplifiers, 82 and 86, as is known in the art.

For arrhythmia detection, the device 10 utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 enables capture detection by triggering the ventricular pulse generator 72 to generate a stimulation pulse, starting a capture detection window using the timing circuitry within the microcontroller 60$k$ and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits shown in FIG. 1. For the stimulation device 10, which employs shocking therapy, the battery must be capable of operating at low current drains for long periods of time and then be capable of providing high-current pulses (for capacitor charging) when the patient requires a shock pulse. The battery 114 must also have a predictable discharge characteristic so that elective replacement time can be detected. Accordingly, the present invention employs lithium/silver vanadium oxide batteries, as is true for most (if not all) such devices to date.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuits 100.

As further shown in FIG. 1, the present invention preferably includes an impedance measuring circuit 120 which is enabled by the microcontroller 60 by a control signal 122.

The impedance measuring circuit 120 is not critical to the present invention and is shown only for completeness.

It is the primary function of the present invention to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5-10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with RV electrode 36 along, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As may be noted in FIG. 1, the leads 20 and 30 provide a number of evoked response sensing electrode configuration possibilities for detection of either ventricular or atrial evoked responses. Further, as may be understood from the prior description herein, there are a number of different possible pacing configurations which may be employed. The pacing configurations may include, for example, bipolar or unipolar single chamber atrial or ventricular pacing, bipolar pacing in one heart chamber coupled with unipolar pacing in the other heart chamber, or bipolar pacing in both heart chambers. Hence, the pacing configuration is defined by the type of stimulation device, the type of leads, and the electrode implantation sites.

In accordance with the present invention, for each possible pacing configuration, there is stored in the memory 94, a list of one or more available evoked response sensing electrode configurations, for either atrial and/or ventricular evoked response sensing as may be appropriate for the particular pacing configuration. As an example, if bipolar dual chamber pacing is selected, the corresponding ventricular evoked response sensing electrode configuration list may include a first electrode configuration of electrode 24 and electrode 34 and a second electrode configuration of electrode 34 and the case 40. The atrial evoked response sensing electrode configuration list may include a third electrode configuration of electrode 24 and electrode 34 or a fourth electrode configuration of electrode 34 and the case 40. Other electrode configurations may be possible and included. However, to conserve memory space and processing time, the list is preferably limited to the most propitious evoked response sensing electrode configurations. The electrode configuration lists are preferably transmitted to the device 10 from the external device 102 for storage in memory 94 in a manner as previously described.

Figure 2:
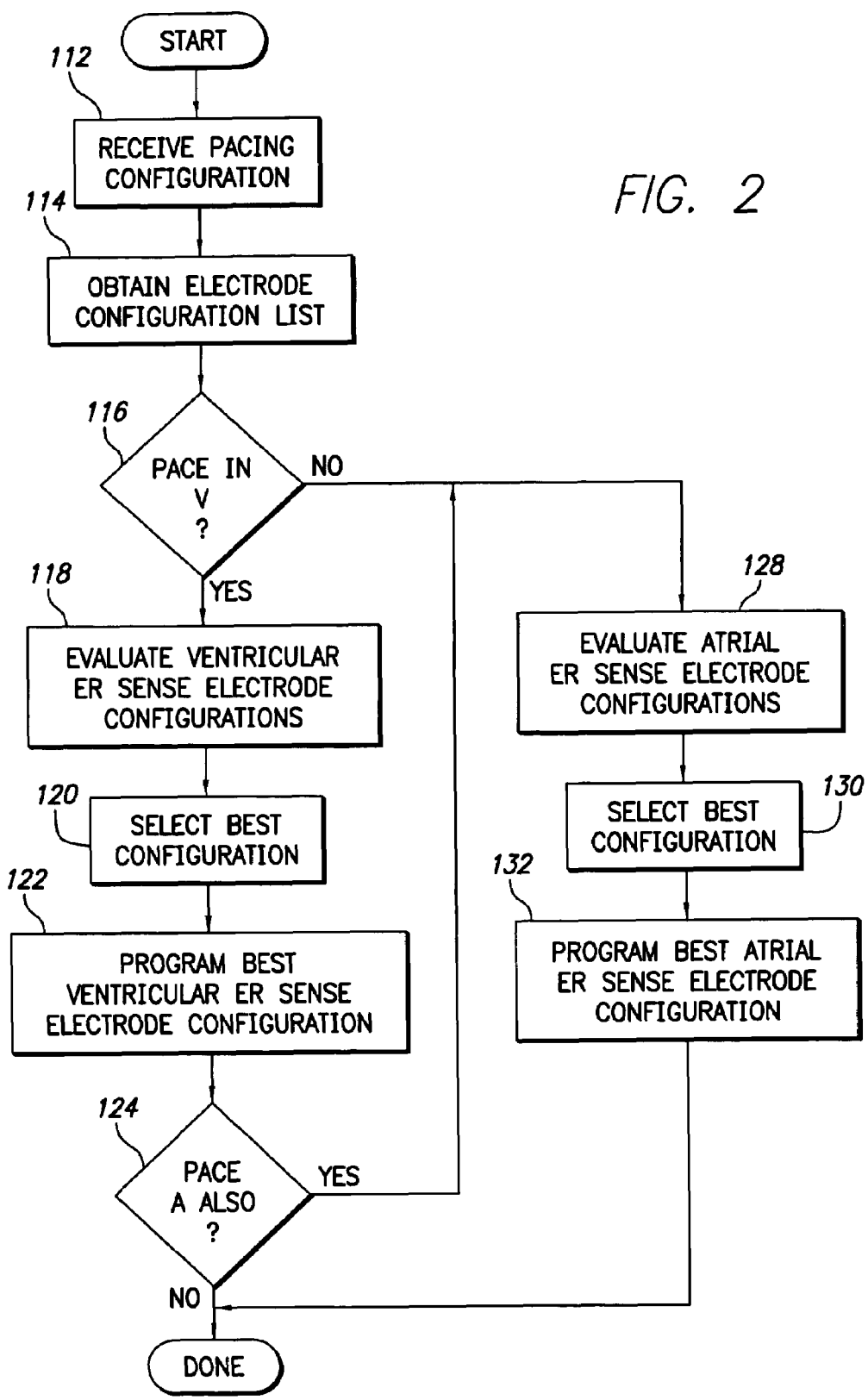
FIG. 2 is a flow chart illustrating an overview of the operation of the present invention.

FIG. 2 is a flow chart providing an overview of a method of selecting an evoked response sensing electrode configuration in accordance with a preferred embodiment of the present invention. The method initiates at an activity block 112 wherein the controller 60 receives the programmed pacing configuration from the external device 102. The programmed pacing configuration is then used in activity block 114 to access the memory 94 for the corresponding evoked response sensing electrode configuration list (if single chamber pacing is programmed) or lists (if dual chamber pacing is programmed).

The method then advances to decision block 116 wherein it is determined if ventricular pacing has been programmed. If the answer is "NO", the method advances to evaluate the listed and available atrial evoked response sensing electrode configurations. If the answer is "YES", the method advances to activity block 118 wherein the listed ventricular evoked response sensing electrode configuration is evaluated.

To evaluate each listed electrode configuration, the switch bank 74 provides each listed electrode configuration to the data acquisition system 90. For each listed configuration, the system 90 senses the evoked response plus polarization resulting from the primary stimulation pulse and then senses the polarization resulting from the backup stimulation pulse delivered during the refractory period following the primary stimulation pulse. The controller then subtracts the polarization from the evoked response plus polarization to derive a factor representing signal-to-noise ratio.

The controller repeats the evaluation process for each listed ventricular evoked response sensing electrode configuration. When activity block 118 is completed, the method advances to activity block 120.

In activity block 120, the controller selects the best evaluated electrode configuration. The electrode configuration selection is based upon signal-to-noise ratio.

The method then advances to activity block 122 wherein the selected ventricular evoked response sensing electrode configuration is automatically programmed in the device 10 by being stored in memory 94. The controller 60 and switch bank 74 will cause the selected configuration to be coupled to the system 90 for future capture and threshold tests. The memory 94 may further be accessed by the external device 102 to advise the physician of the selected electrode configuration.

The method then advances to decision block 124 wherein it is determined if atrial pacing has also been programmed. If the answer is "NO", the process is completed. However, if atrial pacing has been programmed, the method then advances to evaluate the listed available atrial evoked response sensing electrode configurations. To evaluate the listed atrial evoked response sensing electrode configurations, to select the best electrode configuration, and to program the device 10 for the selected atrial evoked response sensing electrode configuration, the controller implements activity blocks 128, 130, and 132. The actions to be taken in activity blocks 128, 130, and 132 are identical to the actions taken in the previously described activity blocks 118, 120, and 122, respectively. The only difference is that the processing is directed to the atrial evoked response sensing electrode configurations. Once the best atrial evoked response sensing electrode configuration has been selected and programmed into the device, the process is completed.

Upon completion of the foregoing process illustrated in FIG. 2, the device 10 will be programmed for using the best available evoked response sensing electrode configurations made available by the particular pacing configuration. In so doing, the microcontroller 60 and switch bank 74 will couple the best evoked response sensing electrode configuration to the data acquisition system 90 when evoked responses are to be sensed. As a result, evoked response sensing may be essentially optimized.

Referring now to FIG. 3, it illustrates, in flow diagram form, the method steps which may be taken by the controller 60 to evaluate, select, and program a ventricular evoked response sensing electrode configuration for the aforementioned dual chamber bipolar pacing configuration. In this configuration, the ventricles are paced with electrodes 32 and 34 and the atria are paced with electrodes 22 and 24.

The method initiates at an activity step 140 wherein the controller evaluates the atrial ring electrode (electrode 24) to ventricular ring electrode (electrode 34) ventricular evoked response sensing electrode configuration. Here, the controller causes the switch bank 74 to couple electrodes 24 and 34 to the data acquisition system 90. It then evaluates the signal-to-noise ratio for sensing ventricular evoked response between those two electrodes in a manner as previously described.

Next, in activity step 142, the controller is called upon to evaluate the ventricular ring electrode (electrode 34) to case 40 ventricular evoked response electrode configurations. Here, the controller causes the switch bank 74 to couple electrode 34 and the case 40 to the data acquisition system 90. It then evaluates the signal-to-noise ratio for sensing ventricular evoked response between those two electrodes in a manner as previously described.

Next, in decision block 144, the controller 60 compares the determined signal-to-noise ratios to a predetermined standard to determine if any one of the electrode configurations yields an acceptable signal-to-noise ratio. If neither configuration does, the controller, in activity block 146, set a flag to recommend to the physician that ventricular evoked response sensing be programmed off. However, in accordance with decision block 144, if either one or both electrode configuration yields an acceptable signal-to-noise ratio, the controller in activity block 148 selects the electrode configuration providing the best signal-to-noise ratio and programs the device 10 to use the selected electrode configuration for sensing ventricular evoked responses. The method is then completed for evaluating the available ventricular evoked response sensing electrode configuration. It then may proceed to repeat the foregoing process to evaluate the available atrial evoked response sensing electrode configurations. Those electrode configurations, as previously mentioned, include the atrial ring electrode (electrode 24) to ventricular ring electrode (electrode 34) and the atrial ring electrode (electrode 24) to the case 40.

As can be seen from the foregoing, the present invention provides an implantable cardiac stimulation device and method which provides the selection of an optimized evoked response sensing electrode configuration. The process is fully automatic once the available sensing electrode configuration lists are loaded into the memory for each one of the possible pacing configurations. The lists may even take into account the nature of the available sensing electrodes. For example, an electrode which is formed of a polarizing material, such as polished platinum, may be avoided while an electrode formed of a non-polarizing material, such as activated vitreous carbon, titanium nitride, Platonized platinum, iridium oxide and palladium oxide may be incorporated on the list and used to advantage in sensing evoked responses.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. An implantable cardiac stimulation device to apply pacing stimulation pulses to a heart and to sense evoked responses in response to the pacing stimulation pulses, the device comprising:
   at least one cardiac lead adapted for placement in electrical contact with the heart, the at least one lead comprising a plurality of electrodes that define a plurality of pacing configurations and a plurality of sensing configurations for the heart;
   a pulse generator to apply the stimulation pacing pulses to the heart in accordance with a selected one of the pacing configurations;
   a sensor control that maintains lists of potential sensing configurations for each of the pacing configurations, wherein the sensor control is operative to test each sensing configuration in the list for the selected pacing configuration and to automatically select an evoked response sensing electrode configuration from among a plurality of evoked response sensing electrode configurations based on the results of the test, and wherein the plurality of evoked response sensing electrode configurations refers to sensing as a function of electrode implantation sites of the cardiac lead; and
   a sensor to sense the evoked responses with the automatically selected evoked response sensing electrode configuration;
   wherein the sensor control includes an evoked response sensing electrode configuration evaluator that determines which one of the available evoked response sensing electrode configurations has a greatest measure of a predetermined evoked response sensing characteristic; and
   wherein the evaluator determines which one of the available evoked response sensing electrode configurations provides a greatest signal-to-noise ratio.

2. The device of claim 1 wherein each pacing configuration is defined by pacing mode, lead type, and lead implant location.

3. The device of claim 1 wherein the sensor control includes a processor that is programmed to select the evoked response sensing electrode configuration from among the plurality of available evoked response sensing electrode configurations corresponding to the pacing configuration.

4. The device of claim 3 wherein the pulse generator is arranged to apply pacing stimulation pulses to a ventricle of the heart and wherein the processor is programmed to select a ventricular evoked response sensing electrode configuration from among the plurality of available evoked response sensing electrode configurations.

5. The device of claim 3 wherein the pulse generator is arranged to apply pacing stimulation pulses to an atrium of the heart and wherein the processor is programmed to select an atrial evoked response sensing electrode configuration from among the plurality of available evoked response sensing electrode configurations.

6. An implantable cardiac stimulation device to apply pacing stimulation pulses to a heart and to sense evoked responses in response to the pacing stimulation pulses, the device comprising:
   at least one cardiac lead adapted for placement in electrical contact with the heart, the at least one lead comprising a plurality of electrodes that define a plurality of pacing configurations and a plurality of sensing configurations for the heart;

a pulse generator to apply the stimulation pacing pulses to the heart in accordance with a selected one of the pacing configurations;

a sensor control that maintains lists of potential sensing configurations for each of the pacing configurations, wherein the sensor control is operative to test each sensing configuration in the list for the selected pacing configuration and to automatically select an evoked response sensing electrode configuration from among a plurality of evoked response sensing electrode configurations based on the results of the test, and wherein the plurality of evoked response sensing electrode configurations refers to sensing as a function of electrode implantation sites of the cardiac lead; and a sensor to sense the evoked responses with the automatically selected evoked response sensing electrode configuration;

wherein the sensor control includes a processor that is programmed to select the evoked response sensing electrode configuration from among the plurality of available evoked response sensing electrode configurations corresponding to the pacing configuration;

wherein the processor is programmed to measure a sensing characteristic of each of the plurality of available evoked response sensing electrode configurations and to select the evoked response sensing electrode configuration having a greatest sensing characteristic measurement; and wherein the sensing characteristic is signal-to-noise ratio.

7. A method of sensing evoked responses of a heart, the method comprising:

placing at least one cardiac lead in electrical contact with the heart, the at least one cardiac lead comprising a plurality of electrodes that define a plurality of pacing configurations and a plurality of sensing configurations for the heart;

stimulating the heart in accordance with a selected one of the pacing configurations;

maintaining lists of potential sensing configurations for each of the pacing configurations;

testing each sensing configuration in the list corresponding with the selected pacing configuration;

automatically selecting an evoked response sensing electrode configuration from among a plurality of evoked response sensing electrode configurations based on the results of the test, wherein the plurality of evoked response sensing electrode configurations refers to sensing as a function of electrode implantation sites of the at least one cardiac lead; and sensing the evoked responses with the automatically selected evoked response sensing electrode configuration;

wherein the automatically selecting an evoked response sensing electrode configuration comprises determining which one of the available evoked response sensing electrode configurations has a greatest measure of a predetermined evoked response sensing characteristic; and wherein the sensing characteristic is signal-to-noise ratio.

8. The method of claim 7 further comprising:

storing in a memory at least one available evoked response sensing electrode configuration corresponding to each respective one of a plurality of pacing configurations;

wherein the selecting an evoked response sensing electrode configuration comprises selecting from the memory the selected evoked response sensing electrode configuration from the available evoked response electrode configurations corresponding to the pacing configuration.

9. The method of claim 7 wherein each pacing configuration is defined by pacing mode, lead type, and lead implant location.

10. The method of claim 7 wherein the stimulating the heart in accordance with a pacing configuration comprises applying pacing stimulation pulses to a ventricle of the heart and wherein the selecting an evoked response sensing electrode configuration comprises selecting a ventricular evoked response sensing electrode configuration from among the plurality of available evoked response sensing electrode configurations.

11. The method of claim 7 wherein the stimulating the heart in accordance with a pacing configuration comprises applying pacing stimulation pulses to an atrium of the heart and wherein the selecting an evoked response sensing electrode configuration comprises selecting an atrial evoked response sensing electrode configuration from among the plurality of available evoked response sensing electrode configurations.

12. A method of sensing evoked responses of a heart, the method comprising:

placing at least one cardiac lead in electrical contact with the heart, the at least one cardiac lead comprising a plurality of electrodes that define a plurality of pacing configurations and a plurality of sensing configurations for the heart;

stimulating the heart in accordance with a selected one of the pacing configurations;

maintaining lists of potential sensing configurations for each of the pacing configurations;

testing each sensing configuration in the list corresponding with the selected pacing configuration;

automatically selecting an evoked response sensing electrode configuration from among a plurality of evoked response sensing electrode configurations based on the results of the test, wherein the plurality of evoked response sensing electrode configurations refers to sensing as a function of electrode implantation sites of the at least one cardiac lead; and sensing the evoked responses with the automatically selected evoked response sensing electrode configuration;

wherein the selecting an evoked response sensing electrode configuration comprises measuring a sensing characteristic of each of the Plurality of evoked response sensing electrode configurations and selecting an evoked response sensing electrode configuration based on the sensing characteristic of each of the plurality of evoked response sensing electrode configurations; and wherein the sensing characteristic is signal-to-noise ratio.

* * * * *